United States Patent [19]

Pilling et al.

[11] Patent Number: 5,053,405

[45] Date of Patent: Oct. 1, 1991

[54] ANTIANDROGENIC SULFONYLSTEROIDOTHIAZOLES

[75] Inventors: Garry M. Pilling, Nassau; John P. Mallamo, Kinderhook, both of N.Y.

[73] Assignee: Sterling Drug Inc., New York, N.Y.

[21] Appl. No.: 541,662

[22] Filed: Jun. 21, 1990

[51] Int. Cl.$^5$ .......................... A61K 31/58; C07J 71/00
[52] U.S. Cl. ........................................ 514/176; 540/57
[58] Field of Search ........................... 540/57; 514/176

[56]  . References Cited

U.S. PATENT DOCUMENTS

| | | | |
|---|---|---|---|
| 2,813,859 | 11/1957 | Korman | 540/57 |
| 3,076,801 | 2/1963 | Bowers | 540/57 |
| 3,081,228 | 3/1963 | Clinton | 540/57 |
| 4,684,636 | 8/1987 | Christiansen et al. | 540/57 |

OTHER PUBLICATIONS

Doorenbos et al., Journal of Pharmaceutical Sciences, vol. 50, p. 271, 1961.
Dénes et al., Journal of the Chemical Society, Chemical Communications, Sec. D, No. 11, pp. 621, 1969.
March, Advanced Organic Chemistry p. 1089 (1988).

*Primary Examiner*—Robert Gerstl
*Attorney, Agent, or Firm*—Theodore C. Miller; Paul E. Dupont

[57]  ABSTRACT

2'-Alkylsulfonylsteroido[3,2-d]thiazoles, for example 2'-methylsulfonyl-5α-pregn-2-en-20-yno[3,2-d]thiazol-17β-ol, which are useful as antiandrogenic agents, and processes for preparation, method of use and compositions thereof are disclosed.

11 Claims, No Drawings

ANTIANDROGENIC SULFONYLSTEROIDOTHIAZOLES

BACKGROUND OF THE INVENTION

1. Field of the Invention

The invention relates to 2'-alkylsulfonylsteroido[3,2-d]thiazoles, which are useful as antiandrogenic agents, and processes for preparation, method of use and compositions thereof.

2. Information Disclosure Statement

Christiansen et al. U.S. Pat. No. 4,684,636 issued Aug. 4, 1987 describes antiandrogenic sulfonylsteroidopyrazoles including as EXAMPLE 1 the compound having the structural formula

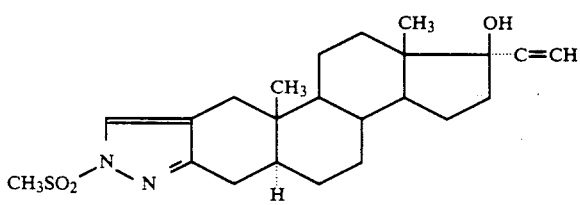

which showed relative binding affinities of 2.1 at 1 hr. and 0.09 at 18 hr. in the rat prostate androgen receptor competition assay and an $AED_{50}$ value of 14 mg./kg. orally in the test for antiandrogenic activity in the castrated immature male rat.

Clinton U.S. Pat. No. 3,081,228 issued Mar. 12, 1963 describes 2'-amino-5α-androst-2-eno[3,2-d]thiazoles having hypotensive activity and having the structural formula

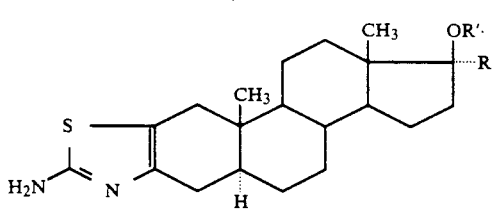

wherein "R represents hydrogen or a lower-alkyl radical, and R' represents hydrogen or a carboxylic acyl radical."

Doorenbos et al. (Journal of Pharmaceutical Sciences, vol. 50, p. 271, 1961) describes the preparation of five 17α-methyl-5α-androst-2-eno[3,2-d]thiazole-17β-ols having the following structural formula but does not describe any biological property thereof.

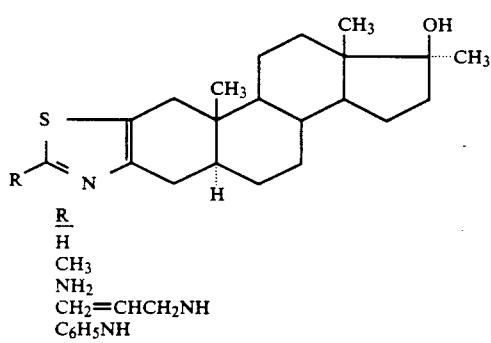

Dénes et al. (Journal of the Chemical Society, Chemical Communications, sec. D, no. 11, p. 621, 1969) describes the preparation of 2'-methyl-5α-cholest-2-eno[3,2-d]thiazole and 2'-methyl-5α-androst-2-eno[3,2-d]thiazol-17β-ol but does not describe any biological property thereof.

SUMMARY OF THE INVENTION

In a first composition of matter aspect the invention is a compound having the structural formula

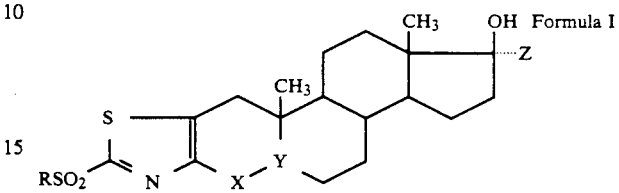

wherein
R is $CH_3$, $CH_3CH_2$, $CH_3CH_2CH_2$ or $(CH_3)_2CH$;
X-Y is

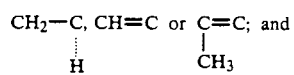

Z is H, $CH_3$, $CH_2CH_3$, C≡CH or CH=$CH_2$.

The compounds of Formula I are useful as antiandrogenic agents.

In a first process aspect the invention is the process of preparing a compound of Formula I which comprises oxidizing with a peroxide the corresponding compound having the structural formula

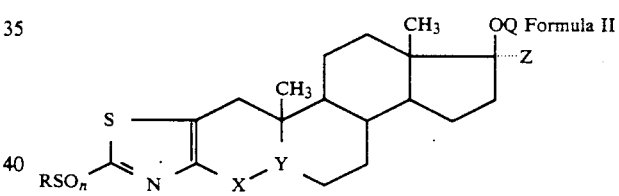

wherein Q is H and n is 0 or 1; or oxidizing with a chromium oxide the corresponding compound of Formula I wherein Z is H and alkylating with the corresponding Z'—Li or Z'—MgCl or Z'—MgBr wherein Z' is $CH_3$, $CH_2CH_3$, C≡CH or CH=$CH_2$ the resulting compound having the structural formula

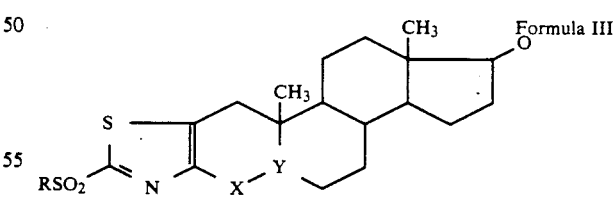

to form the corresponding compound of Formula I wherein Z is Z'; or hydrogenating with a palladium catalyst the corresponding compound of Formula I wherein Z is C≡CH to form the corresponding compound of Formula I wherein Z is CH=$CH_2$ or $CH_2CH_3$.

In a second process aspect the invention is the process for effecting an antiandrogenic response in a mammal which comprises administering to the mammal an antiandrogenically effective amount of a compound of Formula I.

3

In a second composition of matter aspect the invention is a composition which comprises an antiandrogenically effective concentration of a compound of Formula I and a pharmaceutically acceptable vehicle.

DETAILED DESCRIPTION OF THE INVENTION INCLUSIVE OF THE PREFERRED EMBODIMENTS

Preparation of the Compounds

In the preparative process aspect of the invention and the following description "corresponding" means that the variables of the reactants used to prepare a particular compound of Formula I are the same as those of the compound of Formula I.

The peroxide for oxidizing a compound of Formula II to the corresponding compound of Formula I is any peroxide capable of oxidizing RS to $RSO_2$ and is preferably a peroxyacid, most preferably potassium peroxymonosulfate (OXONE). The preferred chromium oxide for oxidizing a compound of Formula I wherein Z is H to the corresponding compound of Formula III is pyridinium chlorochromate. Alternatively the compound of Formula III is prepared by oxidizing the corresponding compound Formula of II wherein Q and Z taken together are a bond, that is wherein the 17-substituent is keto, with a peroxide, preferably potassium peroxymonosulfate (OXONE). All three oxidations are carried out in an inert solvent at a temperature in the range from 0° C. to 100° C. The preferred solvent for the potassium peroxymonosulfate oxidations is aqueous methanol. The preferred solvent for the pyridinium chlorochromate oxidation is dichloromethane. Alkylation of the compound of Formula III with Z'—Li, Z'—MgCl or Z'—MgBr, which are known compounds, is carried out in an ethereal solvent at a temperature in the range from −100° C to 100° C. The preferred ethereal solvent is tetrahydrofuran. The preferred palladium catalyst for hydrogenating C≡CH to CH=$CH_2$ is palladium on strontium carbonate. The preferred solvent therefor is pyridine. The preferred palladium catalyst for hydrogenating C≡CH to $CH_2CH_3$ is palladium on carbon. The preferred solvent therefor is ethanol. Both hydrogenations are carried out at a temperature in the range from 0° C. to 100° C.

The compound of Formula II wherein Q is H and n is 0 is prepared by alkylation of the corresponding compound having the structural formula

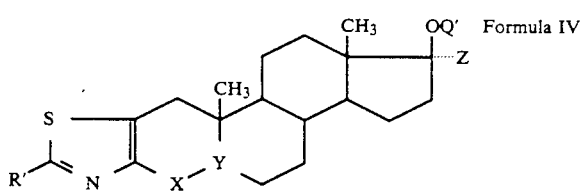

Formula IV wherein Q' is H and R' is HS with RBr or RI in an inert solvent at a temperature in the range from 0° C. to 100° C. The preferred inert solvent is acetonitrile or dimethylformamide. Alternatively and preferably the compound of Formula II wherein Q is H, Z is H and n is 0 and the compound of Formula II wherein Q and Z taken together are a bond (keto) and n is 0 as well are prepared by reaction of the corresponding compound of Formula IV wherein R' is Cl or Br with RSNa formed from RSH and sodium hydride in an inert solvent at a temperature in the range from 0° C. to 100° C. The preferred inert solvent is dimethylformamide.

The compound of Formula II wherein Q is H, n is 0 and Z is Z' is alternatively prepared by alkylation of the corresponding compound of Formula II wherein Q and Z taken together are a bond (keto) and n is 0 with Z'—Li, Z'—MgCl or Z'—MgBr in an ethereal solvent at a temperature in the range from −100° C. to 100° C. The preferred ethereal solvent is tetrahydrofuran. The compound of Formula II wherein Q and Z taken together are a bond and n is 0 is prepared from the corresponding compound of Formula IV wherein R' is Cl or Br by reaction with RSNa formed from RSH and sodium hydride in an inert solvent at a temperature in the range from 0° C. to 100° C. The preferred inert solvent is dimethylformamide.

The compound of Formula II wherein n is 1 is prepared by oxidizing the corresponding compound of Formula II wherein n is 0 with any peroxide capable of oxidizing RS to RSO, preferably a peroxyacid and most preferably potassium peroxymonosulfate (OXONE), in an inert solvent at a temperature in the range from −50° C. to 0° C. The preferred inert solvent is aqueous methanol.

The compound of Formula IV wherein R' is HS and Q' is H and Z is H, or Q' and Z taken together are a bond (keto), is prepared from the corresponding compound of Formula IV wherein R' is Cl or Br by reaction with thiourea in an inert solvent at a temperature in the range from 0° C. to 100° C. and then hydrolyzing the resulting corresponding compound of Formula IV wherein R' is Cl+$(H_2N)_2$C=S+ with alcoholic or aqueous alcoholic alkali at a temperature in the range from 0° C. to 100° C. The preferred alkali is sodium hydroxide. The preferred alcohol of the alcoholic or aqueous alcoholic solvent is methanol.

The compound of Formula IV wherein R' is HS, Q' is H and Z is Z' is alternatively prepared by alkylation of the corresponding compound of Formula IV wherein R' is HS and Q' and Z taken together are a bond (keto) with Z'—Li, Z'—MgCl or Z'—MgBr in an ethereal solvent at a temperature in the range from −100° to 100° C. The preferred ethereal solvent is tetrahydrofuran.

The compound of Formula IV wherein R' is Cl or Br and Q' is H or $COCH_3$ and Z is H, or Q' and Z taken together are a bond (keto), is prepared from the corresponding compound having the structural formula

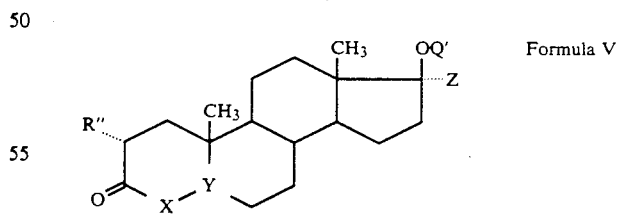

Formula V wherein R'' is NCS and Q' is $COCH_3$ and Z is H, or Q' and Z taken together are a bond (keto), by reaction with hydrogen chloride or hydrogen bromide respectively in an inert solvent at a temperature in the range from 0° to 100° C. The preferred inert solvent for use with hydrogen chloride is ether or methanol. The preferred inert solvent for use with hydrogen bromide is acetic acid.

Alternatively the compound of Formula IV wherein R' is Cl or Br and Q' and Z taken together are a bond (keto) is prepared by oxidation of the corresponding compound of Formula IV wherein R' is Cl or Br, Q' is H and Z is H with a chromium oxide, preferably pyridinium chlorochromate, or with dimethylsulfoxide and trifluoroacetic anhydride in an inert solvent at a temperature in the range from −100° C. to 100° C. The preferred inert solvent is dichloromethane.

In the compound of Formula V wherein R" is NCS, Q' is COCH$_3$ and Z is H or the compound of Formula IV wherein R' is Cl or Br, Q' is COCH$_3$ and Z is H, COCH$_3$ is removed with a strong base in an alcoholic or aqueous alcoholic solvent at a temperature in the range from −50° C. to 100° C. to form the corresponding compound of Formula V wherein R" is NCS, Q' is H and Z is H or the corresponding compound of Formula IV wherein R' is Cl or Br, Q' is H and Z is H. The preferred strong base is potassium carbonate. The preferred alcohol of the alcoholic or aqueous alcoholic solvent is methanol.

The compound of Formula V wherein R" is NCS and Q' is COCH$_3$ and Z is H, or Q' and Z taken together are a bond (keto), is prepared from the corresponding compound of Formula V wherein R" is Br by reaction with sodium or potassium thiocyanate in an inert solvent at a temperature in the range from 0° C. to 100° C. The preferred inert solvent is dimethylformamide.

The compounds of Formula V wherein R" is Br and Q' is COCH$_3$ and Z is H, or Q' and Z taken together are a bond (keto), are generally known or are prepared by bromination of the corresponding compounds wherein R' is H.

In the examples set forth below structures of products are inferred from structures of starting materials and expected courses of preparative reactions. Structural confirmation and estimation of purity of starting materials and products are measured by one or more of melting temperature range (m.r.), elemental analysis, infrared (IR) spectral analysis, ultraviolet (UV) spectral analysis, nuclear magnetic resonance (NMR) spectral analysis, gas chromatography (GC), high pressure liquid chromatography (HPLC) medium pressure liquid chromatography (MPLC) and thin layer chromatography (TLC).

EXAMPLE 1

Pil-R-94 (reference deleted in PTO copy)

A. A solution of 17β-acetoxy-2α-bromo-5α-androstan-3-one (the compound of Formula V wherein R" is Br, Q' is COCH$_3$ and Z is H; 75 g.) and sodium thiocyanate (75 g.) in dimethylformamide (750 ml.) was stirred at room temperature for 30 hours then poured with vigorous stirring into icewater. The resulting white solid was collected by filtration and dried affording the compound of Formula V wherein R" is NCS, Q' is COCH$_3$ and Z is H (74.5 g.).

Pil-R-203/Win 58,297 (references deleted in PTO copy)

B. Under nitrogen with stirring at 5° C. hydrogen chloride was bubbled into a solution of part (48 g.) of the product of part A of this example in ether (700 ml.) for 2 hours. The resulting solid product was collected by filtration affording the compound of Formula IV wherein Q' is COCH$_3$, R' is Cl, X-Y is

and Z is H as a solid (42 g., 88% yield for this step and the previous step combined), recrystallization of part of which from acetonitrile gave a white crystalline solid having m.r. 181°–184° C.

Pil-R-40/Win 58,723 (references deleted in PTO copy)

C. A solution of the the product of part B of this example (40.7 g.) and potassium carbonate (13.8 g.) in methanol (400 ml.) and water (40 ml.) was stirred at room temperature for 24 hours then diluted with two volumes of water by dropwise addition. The resulting tan solid was collected by filtration, washed with water and dried affording the compound of Formula IV wherein Q' is H, R' is Cl, X-Y is

and Z is H (34.7 g., 95% yield), recrystallization of part of which from dichloromethane-acetonitrile gave an off-white crystalline solid having m.r. 175°–178° C.

Pil-S-4 (reference deleted in PTO copy)

D. A solution of the product of part C of this example (15 g.) and thiourea (3.35 g.) in acetonitrile (200 ml.) was heated under reflux for 4 hours then poured into water (1.5 l.). The resulting solid was collected by filtration and dried affording the compound of Formula IV wherein Q' is H, R' is Cl$^-$(H$_2$N)C=S$^+$, X-Y is

and Z is H (11.6 g., 64% yield).

Pil-S-5 (reference deleted in PTO copy)

E. A solution of the product of part C of this example (6.5 g.) and sodium hydroxide (2N, 25 ml.) in methanol (100 ml.) was stirred at room temperature overnight. Water was added dropwise to the hazy yellow mixture resulting in a solution which was stirred for 2 hours then poured into ice containing hydrochloric acid (2N, 27.5 ml.). The resulting white solid was collected by filtration, washed with water and dried affording the compound of Formula IV wherein Q is H, R is HS, X-Y is

and Z is H (5.7 g., theoretical yield 5.34 g.).

Pil-S-6 (reference deleted in PTO copy)

F. A mixture of the product of part E of this example (5 g.), iodomethane (0.94 ml.), sodium bicarbonate (1.3 g.) and acetonitrile (75 ml.) was stirred overnight at room temperature. The reaction was shown to be incomplete by TLC. Dimethylformamide (75 ml.) was added, stirring was continued overnight and the mixture was poured into water. The resulting solid was collected by filtration and dried affording a gum. A solution of the gum in chloroform was stripped of chloroform affording the compound of Formula IV wherein Q is H, R' is CH$_3$S, X-Y is

and Z is H as a solid (4.2 g , 81% yield).

Pil-S-13/Win 58,333 (references deleted in PTO copy)

G. With stirring at 5°–15° C. a solution of potassium peroxymonosulfate (OXONE, 49.5%, 14.6 g.) in water (500 ml.) was added to a solution of the product of part F of this example (6 g.) in methanol (100 ml.). The temperature was allowed to rise to and remain at room temperature for 6 hours. The reaction mixture was poured into ice containing saturated aqueous sodium bicarbonate solution. The resulting mixture was extracted with dichloromethane. The dichloromethane extract was dried over magnesium sulfate and stripped of dichloromethane. Purification of the resulting white solid (4.8 g.) by MPLC using ethyl acetate-hexane (1:1) as eluant and by recrystallization from ethyl acetate-hexane afforded the compound of Formula I wherein Q is H, R is H, X-Y is

and Z is H in two crops (2.5 g., 0.70 g.; 49% yield; m.r. 207°–209° C.), whose Chemical Abstracts name is considered to be 2'-methylsulfonyl-5α-androst-2-eno[3,2-d]thiazol-17β-ol.

EXAMPLE 2

Pil-S-102/61,051 (references deleted in PTO copy)

A. A solution of the compound of Formula IV wherein Q' is H, R' is Cl, X-Y is

and Z is H (the product of part C of example 1, 17 g.) and pyridinium chlorochromate (17 g.) in dichloromethane (200 ml.) was stirred at 21°–30° C. for 4 hours then filtered through magnesium silicate (FLORISIL). The filter pad was washed with ethyl acetate-hexane (1:1, 1 l.). The filtrate was stripped of solvents affording the compound of Formula IV wherein Q' and Z taken together are a bond (keto), R' is Cl and X-Y is

(16.3 g., 96% yield, m.r. 218° C.).

Pil-S-165/Win 61,298 (references deleted in PTO copy)

B. Under nitrogen with stirring at −10°–0° C. under a dry ice condenser methanethiol (30 g.) was added during 3 hours to a suspension of sodium hydride (60% in oil, 20 g.) and the product of part A of this example (45.12 g.) in dimethylformamide (1 l.) Stirring was continued for an additional hour, then the mixture was poured into ice (1 l.) containing aqueous sodium hydroxide solution (2N, 1 l.). The resulting off-white solid was collected by filtration, dried and crystallized from isopropyl alcohol affording the compound of Formula II wherein Q and Z taken together are a bond (keto), R is CH₃, X-Y is

and n is 0 in two crops (34.8 g., 4.8 g.; 85% yield uncorrected for a small amount of starting material in the product). Recrystallization of the second crop from dimethylformamide-acetonitrile gave product (2.3 g.) having m.r. 189°–191° C.

Pil-S-142-143/Win 61,152 (references deleted in PTO copy)

C. Under nitrogen with stirring at −75° C. acetylene gas (first passed through a dry ice condenser, then sulfuric acid, then soda lime) was bubbled through dry tetrahydrofuran (700 ml.). A solution of n-butyllithium in hexane (2.2M, 550 ml.) was added dropwise during 2 hours with continued acetylene bubbling. The product of part B of this example (73.4 g.) was then added as a solid. Progress of the reaction was followed by TLC. The temperature was allowed to rise to and remain at −55° C. for 1 hour and then to rise to and remain at room temperature for 30 minutes. The reaction mixture was then poured into ice-water containing ammonium chloride (3 moles). The organic layer was separated. The aqueous layer was extracted twice with dichloromethane. The combined organic layer and dichloromethane extracts were dried over magnesium sulfate and stripped of solvents. The residual off-white solid (89.5 g.) was slurried in hexane affording the compound of Formula II wherein Q is H, R is CH₃, X-Y is

Z is C≡CH and n is 0 as as off-white solid (72.88 g., 93% yield). Concentration of the hexane filtrate gave an oily solid (12.1 g.). Decantation of the oil and recrystallization of the solid from dichloromethane-hexane gave more product (2.17 g., 3% yield, m.r. 194°–195° C.).

D. Under nitrogen with stirring at −10° C. a solution of potassium peroxymonosulfate (OXONE, 49.5%, 194.5 g.) in water (975 ml.) was added dropwise to a solution of the product of part C of this example (72.8 g.) in methanol 1.5 l. When the addition was about 80% complete, TLC showed only sulfoxide and no sulfone. Part (200 ml.) of the reaction mixture was poured with stirring into ice-water (500 ml.). The resulting white solid (7.5 g.) was collected by filtration, dried and recrystallized twice from ethyl acetate affording the compound of Formula II wherein Q is H, R is CH₃, X-Y is

Z is H and n is 1 as a white crystalline solid (1.5 g., 25% yield, m.r. 231°–232° C.).

E. Under nitrogen with stirring at −10° C. a solution of potassium peroxymonosulfate (OXONE, 49.5%, 20 g.) in water (120 ml.) was added dropwise to a suspension of the product of part C of this example (8.6 g.) in methanol (180 ml.). The temperature was allowed to rise to and remain at room temperature overnight. More potassium peroxymonosulfate (OXONE, 49.5%, 3 g.) was added and stirring was continued at room temperature overnight again. Water (250 ml.) was added dropwise. The resulting white solid (8 g.) was collected by filtration, combined with the corresponding product of a previous preparation (3.7 g. from 4 g. of the product of part C of this example) and recrystallized from ethyl acetate-hexane affording the compound of Formula I wherein R is $CH_3$, X-Y is

and Z is C≡CH (8.2 g., 60% yield, m.r. 239°–240° C, whose Chemical Abstracts name is considered to be 2'-methylsulfonyl-5α-pregn-2-en-20-yno[3,2-d]thiazol-17β-ol. More product (3 g., 22% yield) was obtained from the mother liquor.

EXAMPLE 3

A mixture of a solution of the product of part E of example 2 (2.8 g.) in ethyl acetate (150 ml.) and palladium on carbon (10%, 0.5 g.) was hydrogenated with mechanical shaking under pressure (from 40 to 15 p.s.i.g.). The mixture was filtered and the filtrate wa stripped of solvent. Recrystallization of the residue (2.8 g.) from ethyl acetate-hexane afforded the compound of Formula I wherein R is $CH_3$, X-Y is

and Z is $CH_2CH_3$ as a white crystalline solid in two crops (1.5 g., 300 mg.; 64% yield; m.r. 188° C.), whose Chemical Abstracts name is considered to be 2'-methylsulfonyl-5α-pregn-2-eno[3,2-d]thiazol-17β-ol.

Antiandrogenic Properties of the Compounds

Utility of the compounds of Formula I as antiandrogenic agents was evaluated in two tests, the in vitro rat prostate androgen receptor competition assay and the in vivo test for antiandrogenic activity in the castrated immature male rat.

In the rat prostate androgen receptor competition assay prostate glands from 24 hr. castrated adult male rats weighing approximately 250 g. were homogenized in aqueous pH 7.4 buffer containing triaziquone (10 mM), sodium molybdate (20 mM), 1,4-dithiothreitol (2.0 mM) and glycerol (10%). The homogenate was centrifuged at the equivalent of 105,000 g. for 1 hr. Aliquots of the supernatant liquid (cytosol) were incubated with methyltrienolone labelled with tritium in the 17α-methyl (5 nM final concentration) in either the absence or presence of increasing concentrations ($10^{-9}$–$10^{-5}$M) of unlabelled methyltrienolone as a reference or of a test compound for 1 hr. or overnight (approximately 18 hr.) at 4.C. Triamcinolone acetonide (1 μM) was added to the cytosol before incubation to block the low affinity binding of labelled methyltrienolone to progesterone and glucocorticoid receptors. After the 1 hr. or 18 hr. incubation period an aqueous suspension of dextran (T-70, 0.05%)-coated charcoal (1%) was added to the incubation mixture and incubation was continued for 5 min. The incubation mixture was centrifuged to remove charcoal (nonprotein)-bound labelled methyltrienolone. The supernatant was separated and its radioactivity was counted to determine the concentration of protein-bound labelled methyltrienolone. The relative binding affinity was calculated as the concentration of test compound required to reduce the concentration of protein-bound labelled methyltrienolone by 50% as a percentage relative to unlabelled methyltrienolone. Androgens including the naturally occurring testosterone and 5α-dihydrotestosterone (stanolone) and the synthetic methyltrienolone and stanozolol show high relative binding affinities and 1 hr./18 hr. relative binding affinity ratios close to unity. In general antiandrogens including flutamide and cyproterone acetate show lower relative binding affinities and 1 hr./18 hr. relative binding affinity ratios greater than 10.

In the test for antiandrogenic activity in the castrated immature male rat weanling male rats were castrated and, beginning one week later, grouped by body weight and medicated orally with an ethanol (10%)-cottonseed oil suspension of test compound and testosterone propionate (0.8 mg./kg.) for 10 consecutive days. On the day following the last medication the rats were weighed and sacrificed. The ventral prostate gland, seminal vesicles and levator ani muscle of each rat were removed, blotted and weighed. Antiandrogenic potency is defined as the $AED_{50}$, which is the approximate dose of test compound required to inhibit testosterone propionate stimulated prostate weight gain by 50%. Test compounds which did not inhibit prostate weight gain by 50% but nevertheless showed significant (P<0.01) inhibition at a dose of 100 mg./kg. are considered active and are assigned an $AED_{50}$ value of >100.

The following results were obtained.

| Product of Example | Relative Binding Affinity | | Antiandrogenic Potency $AED_{50}$ (mg./kg. Orally) |
| --- | --- | --- | --- |
| | 1 Hr. | 18 Hr. | |
| 1G | 11 | 1.4 | >25 |
| 2E | 0.9 | 0.08 | 17 |
| 3 | 0.8 | 0.09 | 31 |

In the process of effecting an antiandrogenic response in a mammal the antiandrogenically effective amount of the compound of Formula I can be estimated from the foregoing test results. This aspect of the invention is contemplated to be carried out in any mammal having a disease or disorder reversible by use of an antiandrogenic agent, preferably in the human male in the treatment of benign prostatic hypertrophy or prostatic cancer or in the human female in the treatment of polycystic ovarian disease or both or in other human disease or metabolic disorder amenable to treatment with an antiandrogenic agent. It can be carried out using the compound of Formula I alone, but is preferably carried out using a composition comprising the compound of Formula I and a pharmaceutically acceptable vehicle.

The Compositions

The compositions in accordance with the second composition of matter aspect of the invention can be prepared for oral, parenteral, rectal or vaginal administration and can be in solid or liquid dosage form including capsules, tablets, suppositories, solutions, suspensions and emulsions. Conventional pharmaceutically acceptable vehicles and techniques are used in preparing these dosage forms.

We claim:

1. A compound having the structural formula

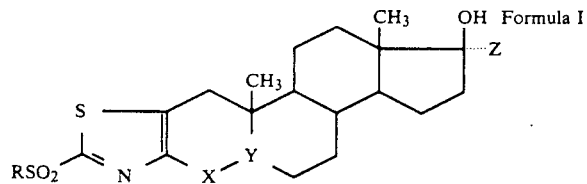

wherein

R is $CH_3$, $CH_3CH_2$, $CH_3CH_2CH_2$ or $(CH_3)_2CH$;

X-Y is

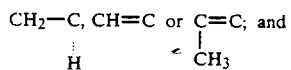

Z is H, $CH_3$, $CH_2CH_3$, $C\equiv CH$ or $CH=CH_2$.

2. A compound according to claim 1 wherein X-Y is

3. A compound according to claim 2 wherein R is $CH_3$.

4. 2'-Methylsulfonyl-5α-androst-2-eno[3,2-d]thiazol-17β-ol according to claim 3.

5. 2'-Methylsulfonyl-5α-pregn-2-en-20-yno[3,2-d]thiazol-17β-ol according to claim 3.

6. 2'-Methylsulfonyl-5α-pregn-2-eno[3,2-d]thiazol-17β-ol according to claim 3.

7. The process for effecting an antiandrogenic response in a mammal which comprises administering to the mammal an antiandrogenically effective amount of a compound of Formula I according to claim 1.

8. The process for effecting an antiandrogenic response in a mammal which comprises administering to the mammal an antiandrogenically effective amount of a compound of Formula I according to claim 4.

9. The process for effecting an antiandrogenic response in a mammal which comprises administering to the mammal an antiandrogenically effective amount of a compound of Formula I according to claim 5.

10. The process for effecting an antiandrogenic response in a mammal which comprises administering to the mammal an antiandrogenically effective amount of a compound of Formula I according to claim 6.

11. A composition which comprises an antiandrogenically effective concentration of a compound of Formula I according to claim 1 and a pharmaceutically acceptable vehicle.

* * * * *